United States Patent
Wu et al.

(10) Patent No.: US 8,816,094 B2
(45) Date of Patent: Aug. 26, 2014

(54) HYDROTHIOLATION OF UNACTIVATED ALKENES

(75) Inventors: Jimmy Wu, Hanover, NH (US); Markku A. Savolainen, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/877,507

(22) PCT Filed: Sep. 28, 2011

(86) PCT No.: PCT/US2011/053571
§ 371 (c)(1),
(2), (4) Date: Apr. 3, 2013

(87) PCT Pub. No.: WO2012/047686
PCT Pub. Date: Apr. 12, 2012

(65) Prior Publication Data
US 2013/0190505 A1      Jul. 25, 2013

Related U.S. Application Data

(60) Provisional application No. 61/389,804, filed on Oct. 5, 2010.

(51) Int. Cl.
*C07C 319/18* (2006.01)
*C07D 257/04* (2006.01)
*B01J 27/125* (2006.01)
*C07C 319/16* (2006.01)
*C07F 9/165* (2006.01)
*C07F 9/18* (2006.01)
*C07B 45/06* (2006.01)

(52) U.S. Cl.
CPC ............ *B01J 27/125* (2013.01); *C07C 319/16* (2013.01); *C07D 257/04* (2013.01); *C07F 9/1653* (2013.01); *C07C 319/18* (2013.01); *C07F 9/18* (2013.01); *C07B 45/06* (2013.01)
USPC ........................................... 548/251; 568/58

(58) Field of Classification Search
None
See application file for complete search history.

(56) References Cited

U.S. PATENT DOCUMENTS 4,721,559 A      1/1988 Olah ............................. 208/135

FOREIGN PATENT DOCUMENTS

WO      WO 2007/007084      1/2007

OTHER PUBLICATIONS

Belley, M. and Zamboni, R. "Addition of Thiols to Styrenes: Formation of Benzylic Thioethers" Journal of Organic Chemistry 1989 54:1230-1232.
Coulombel et al. "Lewis Super-Acid Catalyzed Cyclizations: A New Route to Fragrance Compounds" Chemistry & Biodiversity 2008 5:1070-1082.
Mukaiyama et al. "Addition Reaction of Thiol to Olefin by the Use of $TiCl_4$" Chemistry Letters 1973:355-356.
Screttas. C.G. and Micha-Screttas, M. "Markownikoff Two-Step Hydrolithiation of α-Olefins. Transformation of Secondary and Tertiary Alkyl Phenyl Sulfides to the Relevant Alkyllithium Reagents" Journal of Organic Chemistry 1979 44(5):713-719.
Weïwer, M. and Duñach, E. "Indium(III)-Catalysed Highly Regioselective Addition of Thiolacetic Acid to Non-Activated Olefins" Tetrahedron Letters 2006 47:287-289.
Weïwer et al. "Regioselective Indium(III) Trifluoromethanesulfonate-Catalyzed Hydrothiolation of Non-Activated Olefins" Chemistry Communications 2006 3:332-334.
Weïwer et al. "Indium Triflate-Catalysed Addition of Thio Compounds to Camphene: A Novel Route to 2,3,3-Trimethyl-2-thiobicyclo[2.2.1]heptane Derivatives" European Journal of Organic Chemistry 2007 15:2464-2469.
International Search Report from PCT/US2011/053571, Feb. 21, 2012, PCT.
International Preliminary Report on Patentability from PCT/US2011/05371, Apr. 18, 2013, PCT.

*Primary Examiner* — Alicia L Otton
(74) *Attorney, Agent, or Firm* — Licata & Tyrrell P.C.

(57) ABSTRACT

The present invention is a method for promoting hydrothiolation of an unactivated alkenes with a thiol using gallium triflate.

4 Claims, No Drawings

HYDROTHIOLATION OF UNACTIVATED ALKENES

This patent application is a U.S. National Stage Application of PCT/US2011/053571 filed Sep. 28, 2011 and claims the benefit of priority from U.S. Provisional Application Ser. No. 61/389,804 filed Oct. 5, 2010, the contents of each of which is incorporated herein by reference in their entirety.

BACKGROUND OF THE INVENTION

Hydrothiolation processes such as the thiol-ene reaction have been known for over a century (Dondoni (2008) *Angew. Chem. Int. Ed.* 47:8995-8997; Posner (1905) *Ber. Deut. Chem. Ges.* 38:646-657). Because these reactions proceed via radical intermediates, anti-Markovnikov selectivity is usually observed. However, obtaining Markovnikov addition products still represents a significant challenge. Transition metal-promoted hydrothiolations of unactivated alkynes are known (Weiss, et al. (2009) *J. Am. Chem. Soc.* 131:2062-2063; Cao, et al. (2005) *J. Am. Chem. Soc.* 127:17614-17615; Ananikov, et al. (2005) *Adv. Synth. Catal.* 347:1993-2001; Kondoh, et al. (2005) *J. Org. Chem.* 70:6468-6473; Kondoh, et al. (2007) *Org. Lett.* 9:1383-1385; Malyshev, et al. (2006) *Organometallics* 25:4462-4470), but are relatively rare because sulfur can often act as a poison for these catalysts (Kondo & Mitsudo (2000) *Chem. Rev.* 100:3205-3220). Even fewer reports of the corresponding hydrothiolation of unactivated alkenes have been described. These systems are stoichiometric in metal (Belley & Zamboni (1989) *J. Org. Chem.* 54:1230-1232; Mukaiyama, et al. (1973) *Chem. Lett.* pg. 355-356), require the use of very strong protic acids (Screttas, et al. (1979) *J. Org. Chem.* 44:713-719), or Montmorillonite K-10 clay (Kanagasabapathy, et al. (2001) *Tetrahedron Lett.* 42:3791-3794). A catalytic system in which a Lewis acid was able to promote the hydrothiolation of an alkene has been described (Weïwer & Duñach (2006) *Tetrahedron Lett.* 47:287-289; Weïwer, et al. (2006) *Chem. Commun.* pg. 332-334; Weïwer, et al. (2007) *Eur. J. Org. Chem.* pg. 2464-2469). It was shown that, under reflux, In(III) salts are capable of catalyzing hydrothiolation reactions between thioacetic acid and a variety of alkenes in a Markovnikov fashion (Weïwer & Duñach (2006) supra). Addition of thiols and thioacids to non-activated olefins by $Al^{III}$ and $In^{III}$ have also been described (Coulombel, et al. (2008) *Chem. Biodiver.* 5:1070-1082).

WO 2007/007084 further teaches a process for the addition of a nucleophile such as an acid, alcohol, amine or thiol, to an alkene using the transition metal copper (II) as catalyst. While this reference demonstrates the use of $Cu(OTF)_2$ in combination with oxygen and nitrogen nucleophiles, hydrothiolation reactions using $Cu(OTf)_2$ were not demonstrated.

SUMMARY OF THE INVENTION

The present invention is a method for promoting hydrothiolation of an unactivated alkenes by contacting an unactivated alkene with a thiol in the presence of gallium triflate. In certain embodiments, the method further includes the use of a Brønsted acid such as trifluoroacetic acid as a stoichiometric additive.

DETAILED DESCRIPTION OF THE INVENTION

Conventional methods for preparing sulfones proceed via Mitsunobu reaction of the corresponding alcohol followed by oxidation (Scheme 1; 1->3->4). However, the Mitsunobu reaction is an inherently non-atom economical process which produces stoichiometric amounts of hydrazine dicarboxylate and triphenylphosphine oxide by-products, of which the latter can sometimes be difficult to separate from the final product.

SCHEME 1

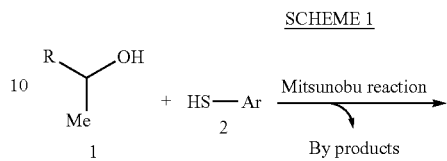

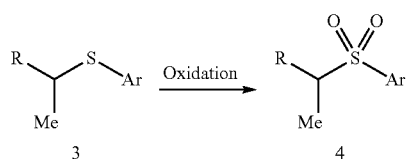

It has now been demonstrated that catalytic $Ga(OTf)_3$ and trifluoroacetic acid (TFA), as a stoichiometric additive, promotes the hydrothiolation of unactivated alkenes with various thiols (Scheme 2). The desired products are obtained in high yield with excellent selectivity for Markovnikov products.

SCHEME 2

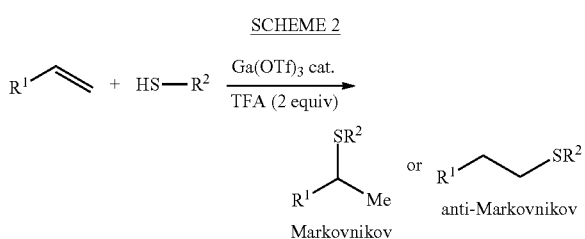

The present invention finds application in the synthesis of sulfones commonly utilized in the modified Julia olefination reaction (Blakemore (2002) *J. Chem. Soc., Perkin Trans.* 1:2563-2585), a process that has been implemented in numerous syntheses of natural products and pharmaceutical agents for the preparation of stereodefined alkenes (Scheme 3).

SCHEME 3

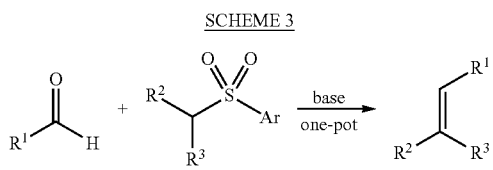

The modified Julia reaction and its variants (i.e., Lythgoe and Kocienski; Blakemore, et al. (1998) *Syn. Lett.* pg. 26-28), are considered to be part of a larger, related group of carbonyl olefination reactions which can provide alkenes with high geometric purity.

The present invention provides a fundamentally different strategy for synthesizing the types of sulfones that are needed in the Julia reaction. The process begins with the Ga(III)-catalyzed hydrothiolation of alkene 5 to provide thioether 3 (Scheme 4). Oxidation of 3 provides the requisite sulfone 4. One of the principal advantages that this invention provides is the flexibility to prepare Julia sulfones (as well as simple thioethers) from alkenes rather than alcohols. Alkenes are ubiquitous functional groups which are typically tolerant to a wider range of reaction conditions than alcohols.

SCHEME 4

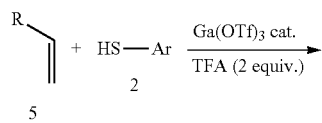

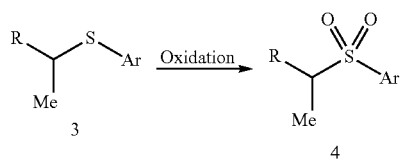

Conditions that provided excellent yields and selectivities were identified for hydrothiolation with phosphorothioic acid 6 (Table 1). Results demonstrate that hydrothiolation with phosphorothioic acid is amenable to substrates possessing α- and β-substituents (7, 8) as well as to cyclic alkenes (11, 13). These results indicate that electron-neutral, -poor, and -rich substrates both perform equally well (9a-9c, 10). Aliphatic alkene 13 was also amenable.

TABLE 1

TABLE 1-continued
| Alkene | Product (yield %)[a] |
|---|---|
| 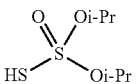<br>10 | 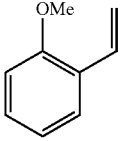<br>17 (72%) |
| 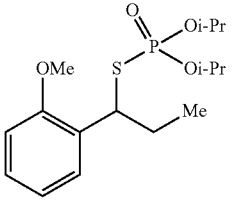<br>11 | 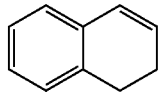<br>18 (68%) |
| 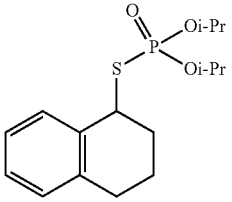<br>12 | 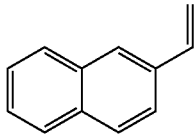<br>19 (82%) |
| 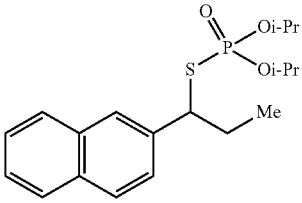<br>13 | 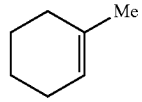<br>20 (77%) |
[a] Isolated yield.

Hydrothiolation of styrene with thiocresol was also demonstrated (Table 2). When a mixture of 21 and 22 was subjected to the optimized conditions, a 3:1 mixture of 23a versus 23b was isolated in low yield (entry 1). When the amount of Ga(OTf)$_3$ was increased to 20%, the yield increased significantly and the anti-Markovnikov product was not observed (entry 3). Special precautions were taken to set up and age the reaction in a darkroom equipped with only a red light. The use of radical inhibitors such as BHT furnished mixed results (entries 2, 4). When the reaction was conducted in the presence of UV light with no Ga(OTf)$_3$, only the undesired anti-Markovnikov product was formed (entry 5). This control reaction established the necessity for the use of Ga(OTf)$_3$ as a catalyst.

TABLE 2

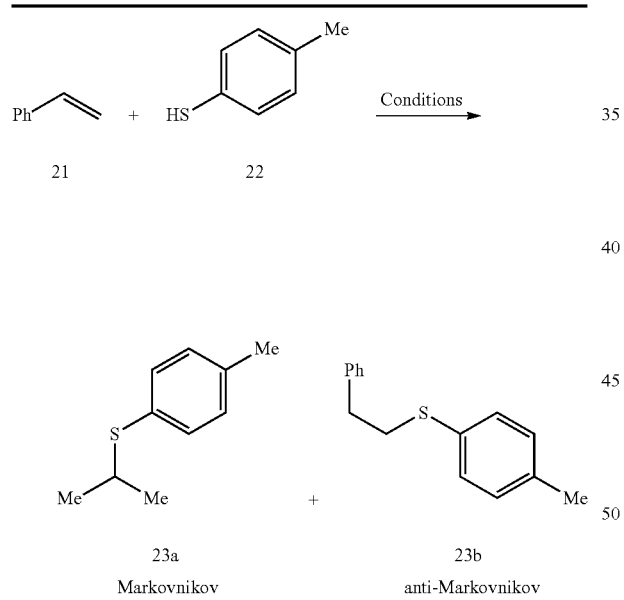

| Entry | Conditions | 23a:23b | Yield (%) |
|---|---|---|---|
| 1 | 5% Ga(OTf)$_3$, 2 equiv TFA | 3:1 | 17[a] |
| 2 | 5% Ga(OTf)$_3$, 2 equiv TFA, 10% BHT | — | —[b] |
| 3 | 20% Ga(OTf)$_3$, 2 equiv TFA | >95:5 | 58[a] |
| 4 | 20% Ga(OTf)$_3$, 2 equiv TFA, 10% BHT | >95:5 | 58[a] |
| 5 | UV (300 nM) | <5:95 | 58[a] |

[a] Isolated yield after m-cpba oxidation to sulfone.
[b] no reaction.

Results indicated that hydrothiolation between styrene (21) and phenyltetrazole 24 was also possible (Scheme 5).

SCHEME 5

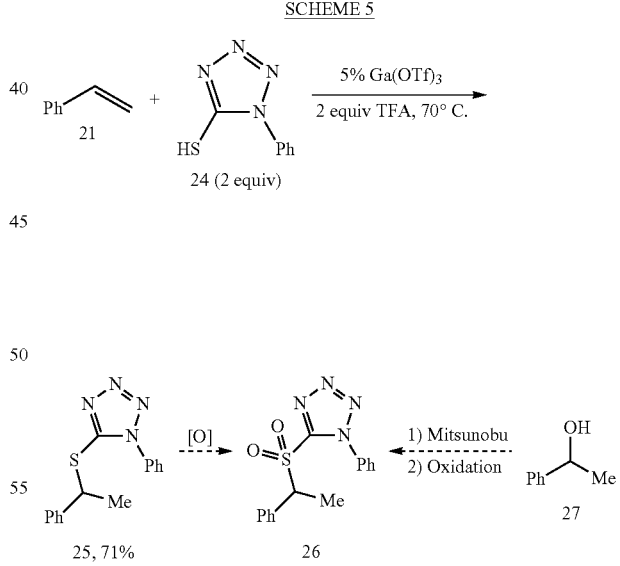

The product 25 was isolated in 71% yield. This result was significant because 25 can be oxidized to sulfone 26 and used in the modified Julia olefination. As described, these sulfones are typically prepared from the corresponding alcohol 27 via Mitsunobu reaction followed by oxidation (Scheme 5).

To further demonstrate the use of phenyltetrazole 24 in the instant method, other substrates were analyzed (Table 3).

TABLE 3

| Olefin | TFA, mol % | Temp, °C. | Yield, % A |
|---|---|---|---|
| styrene | 2 | RT | 79 |
| 4-fluorostyrene | 15 | RT | 82 |
| β-methylstyrene | 2 | 70 | 52 |
| indene | 2 | 4 | 76 |
| 1,2-dihydronaphthalene | 2 | 4 | 66 |
| 4-(trifluoromethyl)styrene | 10 | 70 | 38 |
| 2-methylstyrene | 2 | 70 | 72 |

To further evaluate the instant method, Ga(OTf)$_3$ was compared to other catalysts. The results of this analysis indicated that while indium is in the same group as gallium on the periodic table, Ga(OTf)$_3$ provided significantly higher yields of the desired product (Tables 4 and 5).

TABLE 4

| Catalyst | TFA | Yield (%) |
|---|---|---|
| In(OTf)$_3$ (15%) | None | 44 |
| InBr$_3$ (15%) | None | 46 |
| Bi(OTf)$_3$ (15%) | None | 20 |
| Ga(OTf)$_3$ (15%) | None | 59 |
| Ga(OTf)$_3$ (15%) | 2 equiv | 69 |

Moreover, while TFA and other carboxylic acids are known for use in indirect hydration of branched alkenes (Peterson & Tao (1964) *J. Org. Chem.* 29:2322-2325), nucleophiles of these reactions are used as solvent, not stoichiometrically and only oxygen nucleophiles are described. In this respect, the present invention is distinct as the nucleophile is sulfur and the TFA is used in stoichiometric amounts (Tables 4 and 5).

TABLE 5

| Catalyst | TFA | Yield (%) |
|---|---|---|
| In(OTf)$_3$ (15%) | 2 equiv | 58 |
| InBr$_3$ (15%) | 2 equiv | 57 |
| Ga(OTf)$_3$ (15%) | None | 68 |
| Ga(OTf)$_3$ (15%) | 2 equiv | 79 |

Based upon the results presented herein, the present invention is a method for promoting the hydrothiolation of unactivated alkenes by contacting the unactivated alkene with a thiol in the presence of catalytic Ga(OTf)$_3$. As is conventional in the art, an alkene (also known as an olefin, or olefin) is an unsaturated chemical compound containing at least one carbon-to-carbon double bond (Wade (2006) *Organic Chemistry*, Sixth Ed., Pearson Prentice Hall. pp. 279). The term "unactivated alkene" refers to an alkene lacking a radical or functional group.

Suitable alkene substrates that are thiolated in the process of the invention include substituted or unsubstituted, branched or unbranched alkenes having 3-30 carbon atoms. Alkyl branched cyclic alkenes (e.g., branched cycloolefins) are also useful. The source of the alkene can be any commercial source available, and can be used in crude mixtures or at any level of refinement, any fraction containing alkenes, and at any purity. The results demonstrate that Ga(OTf)$_3$ can catalyze the hydrothiolation of several alkenes. While the majority of alkenes utilized in Table 1 possessed an aromatic substituent at the double bond, alkyl substituted alkene 13 was also shown to be of use in the instant method. Accordingly, mono-, di-, and tri-substituted alkenes possessing both aromatic and alkyl substituents at the double bond can also be thiolated using the instant method as can alkenes with functional groups such as esters, ketones, aldehydes, halides, nitriles, amides, and thioesters. Exemplary alkenes of the invention include, but are not limited to, ethylene, propylene, 1-butene, 2-butene, 1-pentene, 2-pentene, isopentene, hexene-1,2-hexene, 3-hexene, 4-methylpentene-1,2-methylpentene-1,4-methylbutene-1,1-heptene, 2-heptene, 3-heptene, 1-octene, 2-octene, 2-methylheptene-1,4-octene, 3,4-dimethyl-3-hexene, 1-decene, and 1-dodecene, and so forth up to 32 carbon atoms; diener and trienes including butadiene, 1,3-pentadiene, 1,4-pentadiene, 1,3-hexadiene, 1,4-hexadiene, 1,5-hexadiene, 1,3-cyclohexadiene, 1,4-cyclohexadiene, 1,9-decadiene 1,13-tetradecadiene, 2,6-dimethyl-1,5-heptadiene, 2-methyl-2,7-octadiene, 2,7-dimethyl-2,6-octadiene, 2,3-dimethylbutadiene, ethylidene norbornene, dicyclopentadiene, isoprene, 1,3,7-octaroriene, 1,5,9-decartriene, 4-vinylcyclohexene, vinylcyclohexane; divinylbenzene, and cyclic olefins including cyclopentene, cyclobutene, cyclohexene, 3-methylcyclohexene, cyclooctene, cyclodecene, cyclododecene, η5-cyclohexadienyl, η-cycloheptatriene, η8-cyclooctatetracene tetracyclodecene, octacyclodecene, norbornene, 5-methyl-2-norbornene, 5-ethyl-2-norbornene, 5-isobutyl-2-norbornene, 5,6-dimethyl-2-norbornene, 5,5,6-trimethyl-2-norbornene; and acetylenic compounds such as acetylene, methylacetylene, diacetylene, 1,2-dimethylacetylene, η3-pentenyl, and norbornadiene.

The instant hydrothiolation reaction can be carried out as exemplified herein using free thiols, e.g., thiocresol (22) or phenyltetrazole 24, as well as aromatic and alkyl thiols and thiolacids. In addition, other thiols can be used, e.g., those most commonly utilized in the modified Julia reaction (28-30).

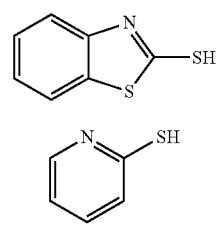

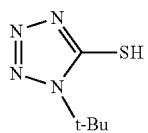

The instant reaction proceeds in a straightforward manner in that an alkene, a catalyst, and a thiol are contacted in a reaction vessel to promote the hydrothiolation of the alkene. While it is generally believed that transition metal centers promote faster reaction rates and more completely convert bonds, it has been surprisingly found that Ga(OTf)$_3$ promotes hydrothiolation of unactivated alkenes more efficiently than transition metals under similar reaction conditions (Tables 4 and 5). Accordingly, the catalyst used in the process of the invention is Ga(OTf)$_3$.

In some embodiments, the instant method is carried out in the presence of the alkene, thiol, and Ga(OTf)$_3$ catalyst. However, the results herein demonstrate that a Brønsted acid such as trifluoroacetic acid (TFA) can significantly accelerate the formation of the Markovnikov product. Accordingly, in other embodiments, the method includes the use of a Brønsted acid additive. Brønsted acids of use in the instant method include, but are not limited to p-toluenesulfonic acid; trifluoromethanesulfonic acid; TFA; camphorsulfonic acid and any other common sulfonic acids; mineral acids such as HCl, HBr and HI; phosphoric acid; perchloric acid; sulfuric acid; nitric acid; carboxylic acids such as acetic acid, benzoic acid, and the like; and hydroxamic acids. In particular embodiments, the Brønsted acid additive is TFA. Desirably, the TFA is used at a stoichiometric amount, i.e., an amount where all reagents are consumed, no shortfall of reagent is present, and the yield is 100%, i.e., no residues remain.

The present method can be carried out under suitable reaction conditions. For example, it may be desirable that the reagent species employed are activated at temperatures above those the reagents would encounter during shipping or storage to ensure storage stability. Accordingly, suitable reaction temperatures range from 0° C. to about 250° C., more preferably from 70° C. to 200° C. Moreover, the reaction time is not limited and can range from 0.5 hours to 48 hours. Further, the reaction can be carried out at any desired pressure. It is also known that UV light promotes the formation of anti-Markovnikov products via the thiol-ene reaction. Although special precautions may be taken to set up and age the hydrothiolation reactions in a darkroom equipped with only a red light, it is possible that the reaction mixture can be exposed to incidental light.

Once the reaction is complete, the hydrothiolated alkene can be separated and isolated from the reaction mixture by distillation, chromatography, or crystallization.

The invention is described in greater detail by the following non-limiting examples.

EXAMPLE 1

Hydrothiolation Using Diisopropyl Phosphorothioic Acid

A reaction vessel equipped with a magnetic stir-bar was charged with dichloromethane, Ga(III) triflate (5 mol %), alkene (1 equiv), phosphorothioic acid (1.2 equiv), and the indicated amount of trifluoroacetic acid. The reaction was aged overnight at room temperature. The reaction was then quenched with saturated aqueous sodium bicarbonate, extracted three times with dichloromethane, washed with brine, dried over sodium sulfate and then concentrated under vacuum. The crude residue was purified using silica gel column chromatography to afford the desired hydrothiolated product.

EXAMPLE 2

Hydrothiolation Using Other Thiols (Including the Julia-Kocieński Thiol)

A reaction vessel equipped with a magnetic stir-bar was charged with dichloromethane, the indicated amount of Ga(III) triflate, thiol (2 equiv), and the indicated amount of trifluoroacetic acid. The mixture was then cooled to 0° C. and brought into a darkroom equipped with a red lamp where the alkene (1 equiv) was added. The reaction vessel was then sequestered from ambient light using aluminum foil, and aged overnight at the indicated temperature. The reaction was then quenched with saturated aqueous sodium bicarbonate, extracted three times with dichloromethane, washed with brine, dried over sodium sulfate, and then concentrated under vacuum. The crude residue was purified using silica gel column chromatography to afford the desired thioether.

What is claimed is:

1. A method for promoting hydrothiolation of an unactivated alkenes comprising contacting an unactivated alkene with a thiol in the presence of gallium triflate thereby promoting hydrothiolation of the unactivated alkenes.

2. The method of claim 1, wherein the unactivated alkene and thiol are further contacted with a Brønsted acid.

3. The method of claim 2, wherein the Brønsted acid is trifluoroacetic acid.

4. The method of claim 2, wherein the Brønsted acid is a stoichiometric additive.

* * * * *